(12) United States Patent
Appling

(10) Patent No.: US 7,618,411 B2
(45) Date of Patent: Nov. 17, 2009

(54) VARIABLE CHARACTERISTIC VENOUS ACCESS CATHETER SHAFT

(75) Inventor: William M. Appling, Granville, NY (US)

(73) Assignee: AngioDynamics, Inc., Queensbury, NY (US)

( * ) Notice: Subject to any disclaimer, the term of this patent is extended or adjusted under 35 U.S.C. 154(b) by 483 days.

(21) Appl. No.: 10/728,267

(22) Filed: Dec. 4, 2003

(65) Prior Publication Data

US 2004/0116901 A1 Jun. 17, 2004

Related U.S. Application Data

(60) Provisional application No. 60/430,998, filed on Dec. 4, 2002.

(51) Int. Cl.
*A61M 25/00* (2006.01)
(52) U.S. Cl. .................................................... 604/523
(58) Field of Classification Search ................ 604/523, 604/525, 524, 529; 138/118, 120, 155
See application file for complete search history.

(56) References Cited

U.S. PATENT DOCUMENTS

| | | | |
|---|---|---|---|
| 5,045,072 A | 9/1991 | Castillo et al. | |
| 5,300,048 A | 4/1994 | Drewes | |
| 5,533,985 A | 7/1996 | Wang | 604/264 |
| 5,542,937 A * | 8/1996 | Chee et al. | 604/523 |
| 5,622,665 A | 4/1997 | Wang | 264/150 |
| 5,725,513 A * | 3/1998 | Ju et al. | 604/527 |
| 5,769,830 A * | 6/1998 | Parker | 604/528 |
| 5,814,016 A | 9/1998 | Valley et al. | |
| 5,895,378 A | 4/1999 | Berenstein et al. | 604/280 |
| 5,908,413 A | 6/1999 | Lange et al. | 604/529 |
| 6,042,578 A * | 3/2000 | Dinh et al. | 604/527 |
| 6,059,769 A | 5/2000 | Lunn et al. | 604/523 |
| 6,135,992 A | 10/2000 | Wang | 604/525 |
| 6,648,024 B2 * | 11/2003 | Wang | 138/177 |

FOREIGN PATENT DOCUMENTS

| | | |
|---|---|---|
| EP | 0 970 715 A2 | 1/2000 |
| EP | 0970715 | 1/2000 |
| WO | WO 99/17827 | 4/1999 |
| WO | WO 2004/050144 | 6/2004 |

* cited by examiner

*Primary Examiner*—Nicholas D Lucchesi
*Assistant Examiner*—Christopher D Koharski

(57) ABSTRACT

A central venous catheter is provided having a proximal tube segment, a distal tube segment and a transition tube segment interposed between the proximal and distal tube segments which are preferably formed as a single integrated tube containing polymer material of different durometer and varying amounts of radiopaque filler material. The polymer durometer of the proximal segment is higher than the polymer durometer of the distal segment. By contrast, the percentage by weight of the filler material contained in the distal segment is higher than that of the proximal segment. The variation in the polymer durometer and the filler amount along the length of the tube provide the desired tensile strength, hardness, chemical resistance and fatigue resistance at the proximal segment and at the same time provide the desired flexibility and radiopacity at the distal segment.

4 Claims, 3 Drawing Sheets

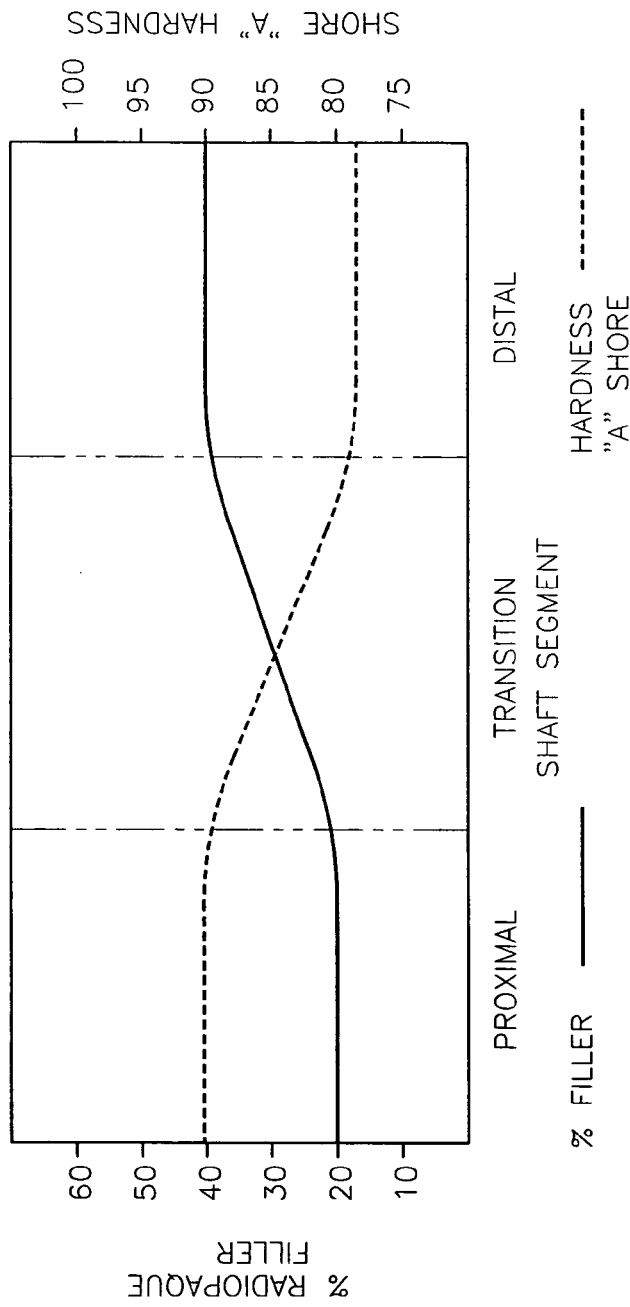

FIG. 3A

| Physical Characteristic | Proximal Segment | | Distal Segment | |
|---|---|---|---|---|
| | Desired | Actual | Desired | Actual |
| Shaft Shore Durometer | Relatively high | 90A | Relatively Low | 78A |
| Radiopaque Filler Level | Minimized | 20% | Maximized | 40% |
| Radiopacity | Not important | Low | Important | High |
| Tensile Strength | High | 6900 psi | Not important | 4700 psi |
| Flexural Modulus | Flexible | 5000 psi | Very Flexible | 1500 psi |
| Chemical Resistance | Maximized | High | Not important | Acceptable |
| Fatigue Resistance | Maximized | High | Not important | Acceptable |

FIG. 3B

VARIABLE CHARACTERISTIC VENOUS ACCESS CATHETER SHAFT

CROSS-REFERENCE TO RELATED APPLICATIONS

This application claims priority to U.S. provisional application No. 60/430,998, filed Dec. 4, 2002, which is incorporated herein by reference.

FIELD OF THE INVENTION

The present invention relates to a medical device apparatus and method for the delivery and withdrawal of fluids and medications. More particularly, the present invention relates to a venous access catheter device with variable shaft characteristics and method of manufacture.

BACKGROUND OF THE INVENTION

Venous access catheters provide venous access to the central circulatory system. Venous access catheters include central venous catheters, dialysis catheters and peripherally inserted central catheters, also known as PICC lines. The access line is used for the delivery of intravenous fluids, medications such as chemotherapy drugs and antibiotics, and blood products. Venous access catheters may also be used as access mechanisms for blood sampling and the administration of contrast agents during diagnostic Computer Tomography (CT) procedures.

One type of venous access catheters, PICC lines, provide venous access to the central circulatory system through a peripheral vein. PICC lines have been in use for many years with a variety of configurations. These include single lumen, dual lumen and other multi-lumen configurations. They come in various lengths to accommodate different anatomy and catheter insertion sites. Generally, a PICC line is inserted through a peripheral location such as the arm, with the tip placed in the central circulation, such as the superior vena cava. The PICC line is designed to remain within the patient for a period of one week to a year and can be accessed in an inpatient, outpatient or home setting.

The majority of the PICC lines presently on the market are made from single material such as silicone rubber or polyurethane. While these catheters are biocompatible and designed to minimize indwelling side effects and optimize patient comfort, they do have several drawbacks. The soft material characteristics of the catheter provide patient comfort but increase insertion difficulties and reduce the long-term durability of the catheter. The material characteristics of the catheter shaft also restrict use to only low pressure injections, typically less than 100 psi.

The PICC line should be sufficiently flexible so that it minimizes patient discomfort and does not cause trauma to the vein wall during insertion or over prolonged periods. On the other hand, it should be rigid enough to facilitate insertion over a guidewire. Pushability and resistance to kinking during and after insertion require a stiffer shaft material. These opposing technical requirements have been partially addressed by some manufacturers by incorporating a softer tip welded to the catheter shaft. While this design provides a soft, atraumatic distal end allowing a stiffer, more rigid shaft body, the catheter is uncomfortable to the patient because the majority of the shaft is stiff. In addition, the physician cannot customize the length of these catheters by cutting at the tip, as is commonly done in the practice.

The PICC line is inserted percutaneously, either under fluoroscopic guidance or using a bedside, "blind" approach followed by x-ray imaging to confirm correct tip placement within the vessel. With either technique, the medical professional must confirm that the distal tip of the PICC line is located within the superior vena cava, rather than in the jugular vein or other unintended vessel. Typically, a post-placement x-ray is used to visualize the distal segment of the catheter within the body. Most venous access catheters do not have sufficient radiopacity to allow for easy visualization of the distal tip.

Some venous access catheter designs have attempted to address this problem by providing a highly radiopaque distal tip bonded to the shaft. The drawback of this enhanced tip design is that it prevents the physician from cutting the tip to customize the length of the PICC line. The design also requires a bond or weld joint, which decreases the overall strength of the catheter and increases the risk of fracture at the bond or weld point.

Other catheter designs have attempted to provide acceptable distal radiopacity levels by using highly filled polymer throughout the entire shaft length. Although providing an acceptable level of visibility, the highly filled shaft material had poor fatigue and chemical resistance, which resulted in an increased occurrence of shaft fracture due to external exposure conditions. The shaft is subject to failure at the proximal end where the catheter exits the body. At the point at which the catheter shaft exits the patient's body, the catheter is exposed to extensive bending, manipulation, and surface contact with site care chemicals such as antibiotics and antiseptics.

Some PICC line designs include a separate obturator or other type stiffener device to provide additional stiffness during insertion. Once inserted and positioned, the obturator is removed from the lumen of the PICC line. While this design has the advantage of ease of insertion, the shaft is soft and not radially strong enough to handle the internal pressures associated with CT injections. In addition, for multi-lumen PICC lines, the medical professional must be cognizant of which lumen to insert the obturator into as incorrect insertion may damage the catheter.

Most PICC lines have a capability of withstanding less than 100 pounds per square inch (psi). This is particularly true of silicone-based PICC lines. Although most PICC line pressure capabilities are sufficient for the delivery of medications and for sampling of blood, they are not designed for delivery of contrast media using a power injector. Power injectors are used in radiology suites as a method for rapidly delivering diagnostic contrast media, particularly for CT applications. Contrast media delivered using a power injector can reach injection pressures of almost 300 psi. Although an in-place PICC line provides an available delivery path for the contrast media, it often cannot be used because the PICC line cannot withstand the higher pressures generated when using a power injector. Instead, the physician must access the patient's vein in another location using a short IV-type catheter designed to withstand higher pressures.

Patients with PICC lines are often very ill and gaining access to a vein is difficult for the caregiver on the one hand while it is as painful and traumatic for the patient on the other hand. Continuous access of the venous system by IV needles or catheters results in eventual destruction of the available veins. Accordingly, being able to access the venous system using an already-in-place PICC line would have significant advantages to both the patient and the health care providers.

Therefore, it is desirable to provide a variable-characteristic venous access catheter that is sufficiently rigid for ease of placement and yet sufficient flexible so as not to damage vessels.

It is also desirable to provide a venous access catheter that is comfortable to the patient and also have sufficient durability including chemical and fatigue resistance to withstand prolonged indwelling times.

It is further desirable to provide a venous access catheter that can withstand higher-pressure injections generated by power infusion devices without causing catheter damage.

It is also desirable to provide a venous access catheter that is designed as a one-piece construction for enhanced reliability and strength.

It is further desirable to provide a venous access catheter with a distal segment having enhanced visibility under X-Ray or fluoroscopy to aid in placement without compromising overall catheter strength.

SUMMARY OF THE DISCLOSURE

According to the principles of the present invention, a central venous catheter having a proximal tube segment, a distal tube segment and a transition tube segment interposed between the proximal and distal tube segments is provided. The three segments are preferably formed as a single integrated tube containing polymer material of different durometer and different amounts of radiopaque filler material. The polymer durometer of the proximal segment is higher than the polymer durometer of the distal segment. By contrast, the percentage by weight of the filler material contained in the distal segment is higher than that of the proximal segment. The variation in the polymer durometer and the filler amount along the length of the tube provides the desired tensile strength, hardness, chemical resistance and fatigue resistance at the proximal segment and at the same time provide the desired flexibility and radiopacity at the distal segment.

In one aspect of the present invention, the transition tube segment contains a mixture of two polymer materials of different durometer.

In another aspect, the durometer of the polymer material contained in the transition tube segment continuously varies over the length of the transition tube segment without any abrupt shift in durometer.

In another aspect, the durometer of the polymer material contained in the transition tube segment continuously decreases from a proximal end of the transition tube segment to a distal end of the transition tube segment.

In another aspect, the percentage by weight of the filler material contained in the transition tube segment continuously varies over the length of the transition tube segment.

In another aspect, the percentage by weight of the filler material contained in the transition tube segment continuously increases from a proximal end of the transition tube segment to a distal end of the transition tube segment.

BRIEF DESCRIPTION OF THE DRAWINGS

FIG. 3A is a graph depicting one method of altering the filler amount and durometer levels of the polymer material to achieve the variable characteristics of the venous access catheter according to the present invention.

FIG. 3B is a table listing the test results of the filler and durometer mixture of FIG. 3A.

DETAILED DESCRIPTION OF THE INVENTION

Figure 1:
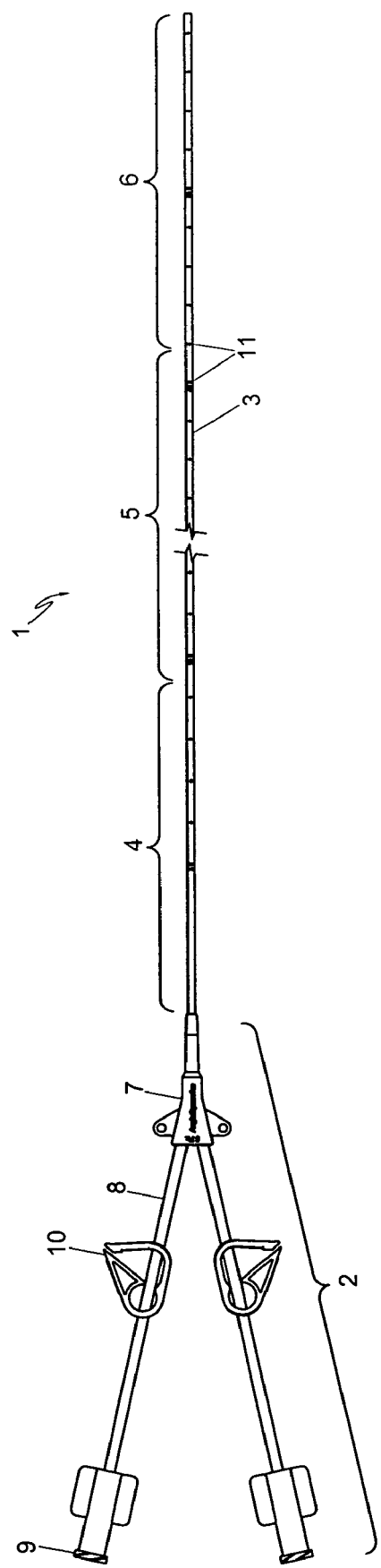
FIG. 1 is a plan view of a venous access catheter according to the present invention.

Referring to FIG. 1, a variable characteristic PICC line of the present invention is shown from a plan view. The catheter 1 is comprised of a hub section 2, a tube or shaft 3 with a substantially rigid proximal segment 4, a transition segment 5 and a substantially flexible distal segment 6. In the embodiment shown, a dual-lumen catheter is provided. In this embodiment, the hub 2 is further comprised of a bifurcated hub component 7 and two extension legs 8 corresponding to each shaft lumen, as is well known in the art. The extension legs 8 terminate at the proximal end with a connector such as a standard luer fitting 9 for connection to injection or aspiration devices. Leg clamps 10 coaxially arranged around the extension legs 8 may be used to clamp off or occlude the leg lumens, preventing the inflow or outflow of fluids through the catheter 1. The catheter may include measurement markers 11 to assist in placement within the vessel.

According to the present invention, a unitary, variable characteristic catheter shaft for a central venous catheter such as a PICC line is provided. Characteristics include varying flexibility along the shaft, increased radiopacity at the distal segment 6 and enhanced tensile strength and durability at the proximal segment 4.

At the proximal segment 4, the shaft is stiff and strong relative to the distal segment 6. Transition segment 5, interposed between proximal segment 4 and distal segment 6, is constructed such that it has more flexibility than proximal segment 4 and less flexibility than distal segment 6. Within transition segment 5, the flexibility may vary from less flexible at the proximal end to more flexible at the distal end. Distal segment 6 is more flexible than transition segment 5 and substantially more flexible than proximal segment 4.

The variable flexibility characteristics of the present invention provides important advantages over conventional PICC lines. The proximal segment 4 of the catheter shaft 3, with its increased rigidity and columnar strength, provides the user with increased pushability and control during insertion and advancement through the vessel. The increased stiffness of the proximal segment 4 relative to the distal segment 6 allows for the line to be inserted and advanced easily with or without the use of a guidewire.

Figure 2:
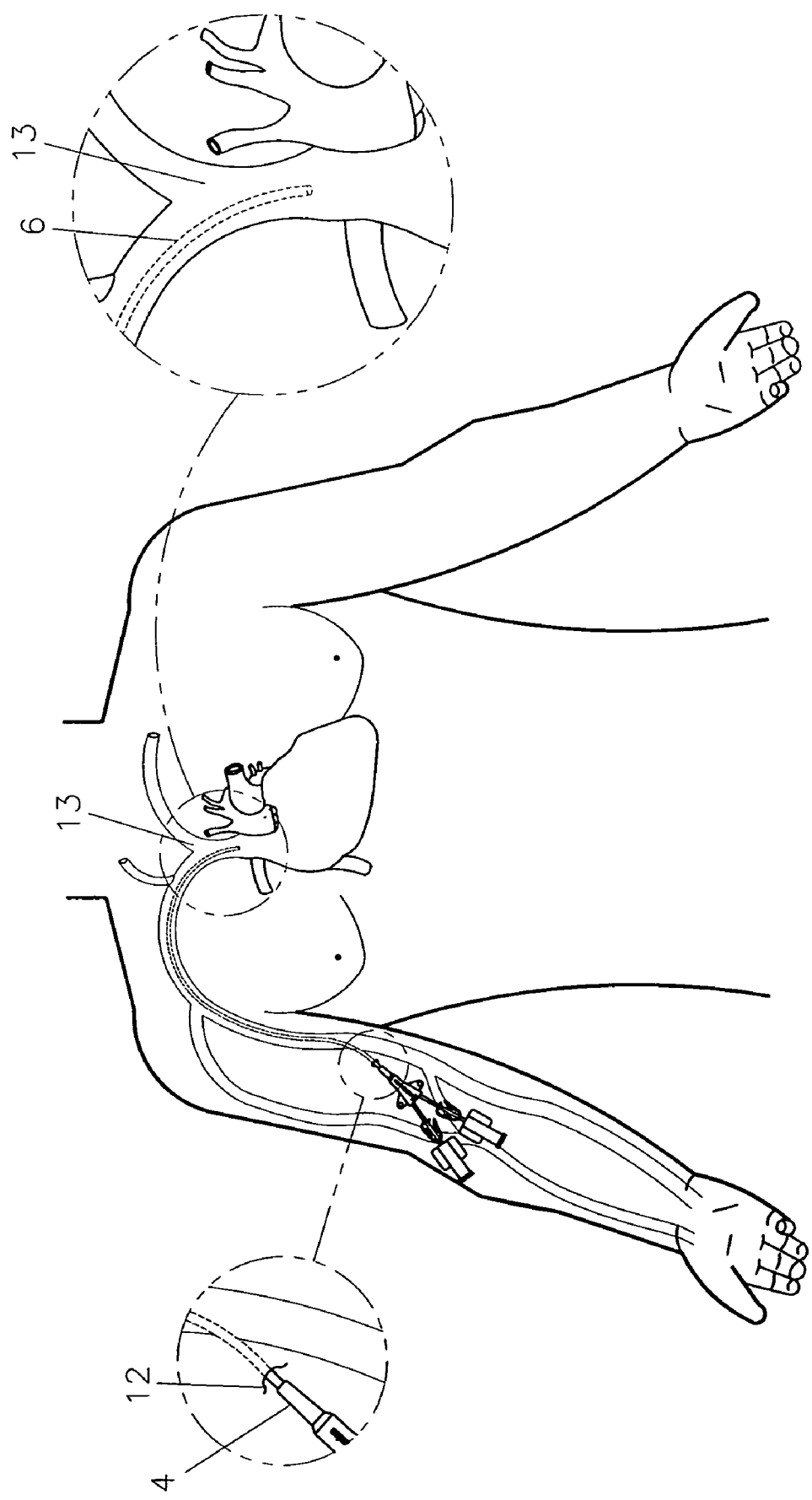
FIG. 2 is a plan view of the venous access catheter of FIG. 1 which has been inserted into a patient and enlarged partial plan views of the proximal and distal segments of the catheter.

The distal segment 6 also provides advantages over traditional PICC lines. The flexible soft shaft at the distal segment 6 is similar to the flexibility of silicone catheters. As such, the shaft minimizes vessel wall trauma caused from contact with the shaft, particularly along distal segment 6 as shown in FIG. 2. Vessel trauma has been shown to increase the risk of thrombus formation, with its resulting complications including catheter occlusion. Decreasing vessel wall trauma over the extended implantation time may contribute to a lower risk of thrombus formation, catheter occlusion and other procedural complications.

In addition to the variable flexibility along the shaft length, the PICC line of the present invention includes enhanced durability and tensile strength at the proximal segment 4. The proximal portion 4 also provides increased strength and durability for that portion of the catheter shaft that is exposed outside of the patient, as shown in FIG. 2. The risks of damage from patient movement, stress at the insertion site 12 and decreased shaft integrity from long-term exposure to chemical substances used during medical procedures are all minimized by providing a stiffer, stronger proximal section 4.

Although implanted PICC lines provide access to the vasculature for administration of fluids, conventional PICC lines typically cannot be used for CT power injections because the shaft cannot withstand the internal pressures generated during the injection, which may be as high as 300 pounds per square inch (psi). CT injections are administered as part of a diagnostic imaging procedure to determine the presence or status of a disease state. A CT power injector is connected to a high-pressure fluid line and then to an access needle. The injections are delivered over a period of time, defined by the flow rate. Typically, contrast media is delivered through an IV needle or catheter at a rate of 2-4 cc per second, with a total delivered volume of between 150 and 200 mls. Although venous access is available through the PICC line, conventional catheters with their relatively low burst strength cannot withstand the prolonged pressure generated during the CT injections. Commonly, PICC lines are accompanied by warnings advising against high-pressure conditions over 100 psi, making them un-usable for the delivery of contrast media during diagnostic imaging procedures.

As a result of the limitations of conventional PICC lines, the physician needs to gain separate access with an IV-type needle. Typically, a needle is placed in the forearm area and is used to inject contrast media during the diagnostic CT procedure. This separate access site increases the complexity and time of the diagnostic procedure in addition to increasing the risks associated with a second access site such as bleeding, hemotomas and infection.

With the present invention, however, CT injections through the PICC line are possible without the risk of catheter failure due to high pressures created during the procedure. The catheter is designed to have a higher radial and tensile strength at the proximal segment 4 than at the distal end 6. Accordingly, the catheter disclosed herein is capable of withstanding higher pressures at the proximal section of the shaft than at the distal segment of the shaft. The peak pressure level during fluid injection of up to 300 psi occurs at the most proximal point of the catheter shaft 3, which has the tensile material characteristics to withstand the higher pressures.

The pressure created by fluid injections drops as fluid travels distally down the shaft, approaching systemic pressure as the fluid enters the target vessel. Because of this decreasing pressure gradient, the distal segment of the PICC line does not have to have the same burst pressure properties as the proximal segment, where the pressure level is higher. Accordingly, the distal segment of the PICC shaft retains its structural integrity during injections even though it has reduced tensile and pressure capabilities.

In addition to the flexural and tensile characteristics of the PICC line of the present invention, the design provides for enhanced visibility of the distal segment 6 under X-ray or fluoroscopic imaging. The enhanced visibility is achieved by increasing the radiopaque filler level relative to the polymer at the distal segment 6 of the catheter. Radiopaque filler materials, usually in the form of a fine powder are normally added to the polymer to increase overall density of the mixture. The increased density serves to block or impede X-ray penetration, thus providing a visual contrast from surrounding tissue and unfilled polymer material. Numerous radiopaque filler materials well known in the art can be used to increase visibility including barium sulfate, tungsten and bismuth salts. Using these radiopaque fillers, physicians can easily visualize the distal segment under X-ray to confirm correct placement within the superior vena cava 13 as shown in FIG. 2.

Turning now to the method of manufacturing the PICC line of the present invention, several different methods can be used to achieve the varying flexural and strength characteristics described above. Stiffness and tensile strength characteristics are a function of the amount of radiopaque filler as well as the selected durometer of the polymer resin. In one aspect of the invention, the shaft tubing may be extruded using differing durometer resins and differing filler ratios within a single extrusion process. Specifically, the shaft tubing may be extruded using a Total Intermittent Extruded (TIE) process well known in the art and described by Daneneau in U.S. Pat. No. 4,888,146, incorporated herein by reference. In that TIE process, two or more different durometer polymer resins are mixed with varying levels of radiopaque filler and then extruded.

Varying only the levels of filler material does not adequately achieve the desired characteristics of a venous access catheter. When only the filler is varied, although the distal end of the catheter is more radiopaque, it is also less flexible at the distal segment due to the increased level of filler. When the durometer by itself is varied, the resulting shaft has the desired flexibility characteristics but is not sufficiently visible under X-ray. With the preferred method of the present invention, the shaft 3 has a first segment 4 of higher durometer resin and less filler, a second segment 5 of mixed durometer resin with higher ratio of filler and a final segment 6 of lower durometer resin with the highest level of filler. With this novel method of varying both the durometer and level of filler throughout the extrusion process, a catheter shaft meeting all the requirements of a PICC line can be produced.

As an illustrative example, a commonly used medical grade polymer material such as Thermal Plastic Urethane (TPU) is available in different durometers with varying percentages of radiopaque filler. In the embodiment shown in FIGS. 3A and 3B, two polymer products can be used. A first polymer is a TPU with a base Shore A hardness of 72A. After 40% radiopaque filler by weight is added to the base polymer, the resulting Shore A durometer is 78A. A second polymer is a TPU with a base Shore A hardness of 87A. After 20% radiopaque filler by weight is added to the base polymer, the Shore A hardness increases to 90A.

Using the TIE process, the first polymer is supplied by a first extrusion device (not shown) for the distal tube segment 6. A second polymer is supplied by a second extrusion device (not shown) for the proximal segment 4. At the transition tube segment 5, the first polymer flow is shut off while the second polymer flow is opened, resulting in a transition tube segment 5 containing a mix of the first and second polymer product. Using the TIE process described above produces extruded tubing with varying physical characteristics based on the polymer resin and filler mix.

FIG. 3A depicts the varying durometer and radiopaque filler along the length of the catheter shaft after extrusion as described above. As can be seen in FIGS. 3A and 3B, at the proximal segment 4 of the tubing, the mixture ratio is approximately 20% radiopaque filler (solid line) and 80% TPU by weight. The filler level increases along the transition tube segment 5 until it reaches approximately 40% filler to 60% TPU at the distal segment 6. Similarly, the TPU durometer, measured in shore A hardness, decreases from 90A at the proximal end to 78A at the distal end. As shown in FIG. 3A, the transition segment of the extruded tubing contains a varying degree of both radiopaque filler and TPU durometer.

Physical test data on the varying characteristic tubing is illustrated in FIG. 3B. At the proximal end of the catheter, the tensile strength of the shaft is high to provide the necessary strength and durability to the exposed segment of the catheter. The higher durometer polymer combined with a lesser amount of radiopaque filler provide the increased strength and durability characteristics of the proximal segment as evidenced by the increased tensile strength measurements. Similarly, the chemical and fatigue resistance levels of the proximal portion of the catheter shaft are higher than at the distal segment.

Although the example above utilizes 20% radiopaque filler at the proximal segment of the catheter, the percentage of radiopaque filler by weight will depend on the density of the filler as well as the specific polymer used. Accordingly, the proximal segment may preferably contain a range of 0% to 30% radiopaque filler by weight. The distal segment filler ratio preferably may range from 30% to 50%. Similarly, the durometer of the combined polymer and filler material will depend on the specific polymer as well as the ratio of filler material to the polymer material. The durometer of the proximal shaft segment 4 may range from 87-100 Shore A hardness while the distal segment may range from 70 to 90 Shore A hardness.

The flexural modulus is a measurement of the relative stiffness of an object under applied stress and is measured in pounds per square inch required to bend the object. The higher the flexural modulus measurement, the higher the stiffness. As shown in FIG. 3B, the proximal portion of the catheter shaft measures a higher flexural modulus psi and is accordingly stiffer than the distal segment of the shaft. The radiopacity of the distal end, with its higher level of filler, results in a shaft that is more visible under X-ray or fluoroscopy at the distal segment. The increased stiffness created by the higher radiopacity filler load at the distal end is offset by the lower durometer resin, resulting in a distal segment that is both highly visible under X-ray and is flexible and atraumatic to the patient.

Thus by varying the durometer and the percentage by weight of the radiopaque filler along the shaft length, optimal characteristics of a venous access catheter can be achieved. At the proximal end of the shaft, where the catheter is subject to increased manipulation and exposure to chemicals, the device is fatigue and chemical resistant as well as having increased overall strength as measured by tensile strength. In addition, the increased strength at the proximal end allows for the safe use of power injections with their relatively high-pressure levels. At the distal end, the shaft has enhanced visibility under image guidance as well as a softer, more flexible atraumatic shaft.

The single extrusion process also ensures a strong transition segment which is less subject to failure under high pressure or tensile force than other welded or bonded transition segments. Accordingly, the absence of welded or bonded points along the catheter shaft will increase durability during insertion, withdrawal and CT injections.

Other methods of creating a variable characteristic PICC line are also possible. For example, the TIE extrusion method previously described can be adjusted to create a transition segment that is longer or shorter relative to the distal and proximal segments. Specifically, by controlling the speed at which the two base polymers are switched during the extrusion process, the length of the transition segment can be varied. Slowing down the switch over rate from the first polymer mix to a second polymer mix will result in a longer transition segment. The rate can be adjusted such that the majority of the shaft consists of the transition segment, thus creating a continuously variable characteristic catheter shaft. Alternatively, increasing the speed at which the conversion from one polymer mix to the other takes place will create a shaft with a relatively short transition segment.

Another method of extrusion, commonly known in the art as co-extrusion, can also be used to create a variable characteristic venous access catheter described herein. Two separate extruders can be utilized to create a single tube with two different material layers. The cross-sectional wall thickness of each layer is then varied along the length of the shaft. As an example, the outer layer may be extruded using the lower durometer polymer, higher radiopaque filler mixture and the inner layer extruded using the higher durometer polymer, lower radiopaque filler mixture. The outer tubing wall thickness transitions from a smaller percentage of the overall tubing wall cross-section to a larger percentage of the overall tubing wall as it approaches the distal end. Conversely, the inner tubing wall thickness transitions from a larger to smaller percentage of the overall tubing wall as it approaches the distal end of the shaft. The resulting single tube would consist of substantially all outer layer material at the distal end of the catheter transitioning to substantially all inner layer material at the proximal end of the catheter. Preferably, the distal segment consists of approximately 90% outer layer with its high radiopacity and relatively low durometer and 10% inner layer, although a range of 75% outer to 95% outer layer is possible. At the proximal segment, the shaft consists of approximately 90% inner layer with its low radiopacity and higher durometer and 10% outer layer. A range of between 75% and 95% inner layer for the proximal segment is acceptable. Although in the example above, the outer layer consisted of the higher filler, lower durometer material, it is possible to reverse this approach and use the higher filler, lower durometer polymer mixture as the inner layer instead. With either method, varying the thickness of each layer of the tubing along the length of the shaft will achieve a continually varying durometer, strength and radiopacity shaft of the optimal venous access catheter.

Alternatively, the relative strength and flexibility of the shaft can also be varied using a cross-linking technique well known in the art. To achieve the varying flexural characteristics within a single shaft, the tubing is extruded using a process combining a cross-linking additive with a polymer. After extrusion, sections of the tubing are exposed to radiation or another thermal energy source. Exposure to radiation creates increased cross-linking of the chemical bonds between the polymer chains. The tubing exposed to the radiation exhibits a higher tensile strength and is less flexible than the non-exposed section of tubing.

Various omissions, modifications, substitutions and changes in the forms and details of the device illustrated and in its operation can be made by those skilled in the art without departing in any way from the spirit of the present invention. Accordingly, the scope of the invention is not limited to the foregoing specification, but instead is given by the appended claims along with their full range of equivalents.

What is claimed is:

1. An integral venous access catheter shaft comprising:
a proximal tube segment of a first polymer material comprising less than 30% by weight radiopaque filler and having a first durometer value between about 87 and 100 Shore A and having a first burst strength of less than 300 psi;
a distal tube segment of a second polymer material comprising between about 30% and 50% by weight radiopaque filler and having a second durometer value between about 70 and 90 Shore A and having a burst strength that is less that the first burst strength, wherein the first durometer value is substantially higher than the second durometer value, and wherein the percentage by weight of said filler in said second polymer material is substantially greater than the percentage by weight of said filler in said first polymer material; and
a transition tube segment between said proximal and distal segments, said transition tube segment having a continuously varying mixture of said first and second polymer materials, wherein the ratio of said first polymer material to said second polymer material continuously decreases from a proximal end to a distal end of said transition tube segment, and wherein the percentage by weight of said filler continuously increases from the proximal end to the distal end of said transition segment, wherein the respective proximal, distal, and transition tube segments are formed by a continuous extrusion process to provide an integral catheter tube without bonds or welds.

2. The catheter shaft of claim 1 wherein said continuous decrease of polymer ratios and continuous increase of filler weight in said transition zone are substantially linear.

3. The catheter shaft of claim 2 wherein the flexibility of the proximal segment is substantially equal to the flexibility at the proximal end of the transition segment and the flexibility of the distal segment is substantially equal to the flexibility of the distal end of the transition segment.

4. The catheter shaft of claim 1 wherein the flexibility of the proximal segment is substantially equal to the flexibility at the proximal end of the transition segment and the flexibility of the distal segment is substantially equal to the flexibility of the distal end of the transition segment.

* * * * *